US009629858B2

(12) United States Patent
Huppert et al.

(10) Patent No.: US 9,629,858 B2
(45) Date of Patent: Apr. 25, 2017

(54) DIALYSIS SOLUTIONS COMPRISING ORGANIC ESTERS OF PHOSPHORIC ACID

(71) Applicant: Fresenius Medical Care Deutschland GmbH, Bad Homburg (DE)

(72) Inventors: Jochen Huppert, Saarbruecken (DE); Pascal Mathis, Bous (DE); Robert Berlich, Sankt Wendel (DE); Robert Pohlmeier, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/182,774

(22) Filed: Jun. 15, 2016

(65) Prior Publication Data

US 2016/0367573 A1 Dec. 22, 2016

(30) Foreign Application Priority Data

Jun. 16, 2015 (DE) ........................ 10 2015 007 842

(51) Int. Cl.
*A61K 31/661* (2006.01)
*A61K 33/10* (2006.01)
*A61M 1/28* (2006.01)
*A61J 1/10* (2006.01)
*B65D 30/22* (2006.01)
*A61M 1/16* (2006.01)
*A61K 33/42* (2006.01)
*A61K 9/08* (2006.01)

(52) U.S. Cl.
CPC ............... *A61K 31/661* (2013.01); *A61J 1/10* (2013.01); *A61K 9/08* (2013.01); *A61K 33/10* (2013.01); *A61K 33/42* (2013.01); *A61M 1/1654* (2013.01); *A61M 1/287* (2013.01); *B65D 31/12* (2013.01)

(58) Field of Classification Search
CPC ...... A61K 31/661; A61K 33/42; A61K 33/10; A61K 9/08; A61M 1/287; A61M 1/1654; A61J 1/10; B65D 31/12
See application file for complete search history.

(56) References Cited

PUBLICATIONS

Chua et al., "Phoxilium vs Hemosol-BO for continuous renal replacement therapy in acute kidney injury", Journal of Critical Care, vol. 28, 2013, 8 pages.
Hui et al., "Evaluation Methods for the Scaling Power of Water", Journal Europeen d'Hydrologie, Vo. 33, No. 1, 2002, 20 pages.
"Sodium Glycerophosphate, Hydrated", European Pharmacopeia 7.0, Corrected 6.6, 2009, 3 pages.

*Primary Examiner* — Ali Soroush
*Assistant Examiner* — Genevieve S Alley
(74) *Attorney, Agent, or Firm* — Fish & Richardson P.C.

(57) ABSTRACT

This document relates to bi-carbonate-buffered dialysis solutions with physiological phosphate content and increased stability. The solutions include an organic ester of phosphoric acid, calcium ions and/or magnesium ions, and optionally additional electrolytes, buffers and glucose in physiologically effective concentrations.

15 Claims, 13 Drawing Sheets

DIALYSIS SOLUTIONS COMPRISING ORGANIC ESTERS OF PHOSPHORIC ACID

CLAIM OF PRIORITY

This application claims the benefit of German Application No. 102015007842.9, filed on Jun. 16, 2015. The entire contents of the foregoing are incorporated herein by reference.

TECHNICAL FIELD

This invention relates to dialysis solutions with increased stability that contain calcium and/or magnesium in addition to phosphate at physiological concentrations.

BACKGROUND

Bicarbonate-buffered dialysis solutions containing calcium ions or magnesium ions typically contain electrolytes, buffers and glucose in physiologically effective concentrations. There is a problem with dialysis solutions which also contain bicarbonate as a buffer in addition to calcium or magnesium in that under certain conditions, in particular at a comparatively high pH and at higher temperatures, carbonates may be formed which are of low solubility, which is unwanted.

Dialysis solutions having a physiological phosphate content are used in acute dialysis to regulate the phosphate balance of patients and to prevent hypophosphatemia. A medically sensible phosphate concentration is in the range from 0.65 to 1.45 mmol/L, or more specifically 0.80 to 1.25 mmol/L, based on experience from clinical application.

If a bicarbonate-buffered dialysis solution containing calcium ions or magnesium ions contains phosphate ions in addition to the bicarbonate ions, there is potentially a risk that phosphate compounds may form which are difficult to dissolve. Due to their low solubility, alkaline earth phosphate precipitations must be classified even more critically from a medical aspect than alkaline earth carbonate precipitations and should therefore be avoided.

A pH increase due to a loss of $CO_2$ by degassing is in particular responsible for the alkaline earth carbonate precipitations and the alkaline earth phosphate precipitations. Under thermodynamic aspects, there is a maximum pH up to which the dialysis solution remains stable, i.e. up to which the named precipitations do not occur. If the pH of the dialysis solution increases under conditions of use such as by the pumping and heating at a dialysis machine or by storage, a metastable state can be achieved. If this state collapses, carbonates and/or phosphates are precipitated which are of low solubility, which can result in considerable complications in the treatment. Magnesium phosphates and calcium phosphates of low solubility in this respect represent the most critical compounds due to the low solubility in basic conditions. However, magnesium carbonate and calcium carbonate also represent critical compounds due to the poor solubility in basic conditions.

It is known from the prior art to prepare bicarbonate-buffered dialysis solutions containing calcium ions or magnesium ions in the form of individual solutions which are received in a dual-chamber bag. This can be realized for solutions which furthermore contain phosphate. A ready-to-use dialysis solution is obtained by mixing the two chamber contents. A separate storage of calcium, on the one hand, and of carbonate or phosphate, on the other hand, and thus an increased stability in the storage of the dialysis solution, can be achieved by the provision of the individual solutions in a dual-chamber bag. It is further known from the prior art to manufacture the bag film from a barrier film to counteract the escape of $CO_2$ and thus the increase in the pH in the individual solution containing bicarbonate and optionally phosphate. Nevertheless, despite this special packaging, the pH of the dialysis solution containing bicarbonate and optionally phosphate increases over the storage time, which has the consequence that on the mixing of the two individual solutions, the pH of the mixed solution, i.e. of the finished dialysis solution, is likewise increased before its use. To avoid precipitations in the mixing or on the use at the dialysis machine, it is best to ensure that the pH of the dialysis solution containing bicarbonate and optionally phosphate and the pH of the mixture manufactured from the individual solutions lie within a relatively narrow framework.

This disclosure provides a bicarbonate-buffered dialysis solution which contains calcium ions or magnesium ions and which generally has a physiological phosphate content such that the probability for the occurrence of precipitations is reduced with respect to known solutions.

SUMMARY

Aspects of this invention are based, in part, on the discovery that it is possible to reduce the occurrence of carbonates and phosphates which have low solubility in a bicarbonate-buffered dialysis solution that contains calcium or magnesium ions and a physiological phosphate content with the addition of an organic ester of phosphoric acid.

In one aspect, the disclosure provides for a dialysis solution that includes bicarbonate ions; one or more of calcium and magnesium ions; and an organic ester of phosphoric acid. In some embodiments of all aspects, the organic ester of orthophosphoric acid is glycerol orthophosphate. In some embodiments of all aspects, the organic ester of orthophosphoric acid is in the form of a salt of the organic ester of orthophosphoric acid. In some embodiments of all aspects, the concentration of the organic ester of phosphoric acid is 0.8 to 1.25 mmol/L with respect to the phosphate. In some embodiments of all aspects, the concentration of the organic ester of phosphoric ester is 1 to 1.2 mmol/L with respect to the phosphate.

In some embodiments of all aspects, the dialysis solution also includes one or more of an electrolyte and an osmotic agent, wherein the electrolyte is selected from the group consisting of sodium ions, potassium ions, and chloride ions, and wherein the osmotic agent is a saccharide or a saccharide derivative. In some embodiments of all aspects, the dialysis solution also includes orthophosphate, wherein the concentration of the orthophosphate is about 0.1 to 0.3 mmol/L. In some embodiments, the concentration of the orthophosphate is about 0.1 to 0.2 mmol/L. In some embodiments of all aspects the dialysis solution also includes one or more of an electrolyte and an osmotic agent, wherein the electrolyte is selected from the group consisting of sodium ions, potassium ions, and chloride ions, and wherein the osmotic agent is a saccharide or a saccharide derivative.

In another aspect, the disclosure provides for a plurality of solution components to be mixed to form a solution, wherein the solution includes: bicarbonate ions; one or more of calcium and magnesium ions; an organic ester of phosphoric acid; and optionally one or more of orthophosphate, an electrolyte, and an osmotic agent. In some embodiments of all aspects, the organic ester of phosphoric acid is in the form of a salt of an organic ester of phosphoric acid. In some embodiments of all aspects, the plurality of solution components include a first solution component and a second solution component, wherein the second solution component comprises the organic ester of phosphoric acid and optionally the orthophosphate. In some embodiments of all aspects, the first solution component is contained in a first chamber of a container, and the second solution component is contained in a second chamber of the container.

In some embodiments of all aspects, the first solution component includes one or more of calcium ions and magnesium ions; and the second solution component does not contain any calcium ions or magnesium ions. In some embodiments of all aspects, the first solution component also includes chloride ions, an osmotic agent and optionally potassium ions; and wherein the second solution component further comprises sodium ions, chloride ions, and bicarbonate ions.

In some embodiments of all aspects, the first solution component does not include any of the following: bicarbonate ions, organic esters of phosphoric acid, orthophosphate and sodium ions. In some embodiments of all aspects, the second solution component does not include any of the following: calcium ions, magnesium ions, potassium ions, and osmotic agents. In some embodiments of all aspects, the first solution component has a pH of about 2.4 to 3.0; and the second solution component has a pH of about 7.0 to 7.8.

In another aspect, the disclosure provides for a multi-chamber bag including two or more chambers, wherein a first chamber comprises a first solution that comprises one or more of calcium ions and magnesium ions; and a second chamber comprises a second solution that comprises an organic ester of phosphoric acid and does not contain calcium ions or magnesium ions.

In some embodiments of all aspects, the second solution also includes an orthophosphate. In some embodiments of all aspects, the first solution also includes chloride ions, an osmotic agent; and the second solution also includes sodium ions, chloride ions, and bicarbonate ions. In some embodiments of all aspects, the first solution also includes potassium ions. In some embodiments of all aspects, the first solution does not contain any of the following: bicarbonate ions, organic esters of phosphoric acid, orthophosphate and sodium ions. In some embodiments of all aspects, the second solution does not contain any of the following: calcium ions, magnesium ions, potassium ions, and osmotic agents. In some embodiments of all aspects, the first solution has a pH of about 2.4 to 3.0; and the second solution has a pH of about 7.0 to 7.8.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other aspects, features, and advantages of the invention will be apparent from the following detailed description and figures, and from the claims.

DETAILED DESCRIPTION

Figure 1:
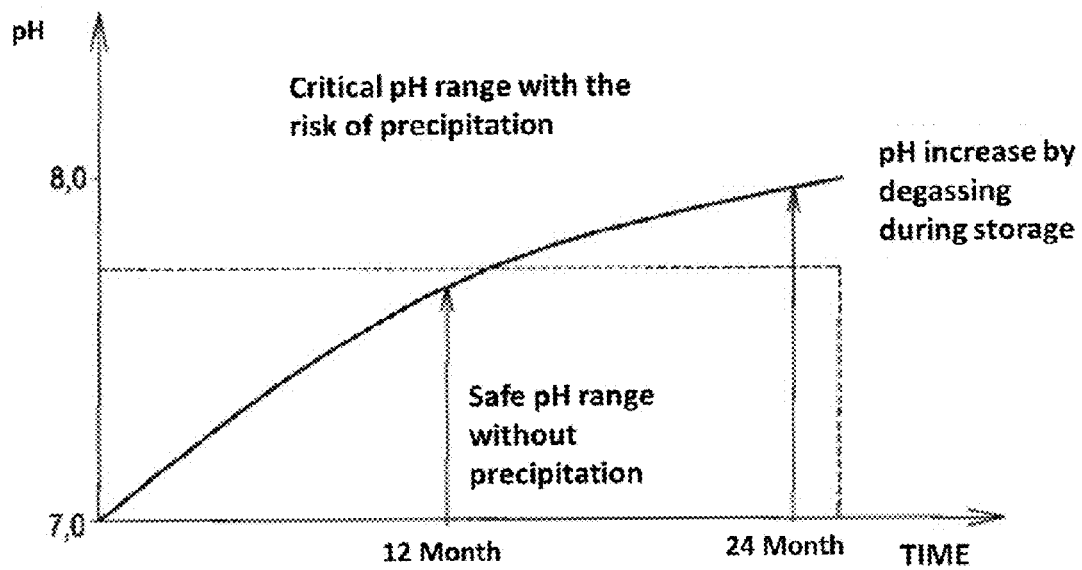
FIG. 1 is a schematic representation of safe and critical pH ranges of a bicarbonate-buffered solution.

Provided herein are bicarbonate-buffered dialysis solutions that contain calcium ions or magnesium ions and that can have a physiological phosphate content such that the probability for the occurrence of precipitations is reduced with respect to known solutions.

Some of the dialysis solutions disclosed herein contain bicarbonate ions as well as calcium ions and/or magnesium ions, and additionally include an organic ester of phosphoric acid.

It has been found that such esters can represent a phosphate source which is absorbed fast by the body, on the one hand, and which does not form any phosphates with low solubility, on the other hand, and which furthermore even stabilizes the solution. The additional stabilization of the dialysis solution or of individual solutions from which the dialysis solution is obtained is believed to be due to the fact that crystal growth of calcium carbonate and/or magnesium carbonate in a dialysis solution of the category is slowed down or even completely inhibited by the presence of the organic ester of phosphoric acid. The upper pH limit at which a precipitation of carbonate takes place is displaced further into basic conditions, i.e. toward higher pH values. Any precipitation reactions then only take place at pH values which are so high they are usually not reached during the dialysis treatment or during the storage of the dialysis solution—optionally divided into individual solutions. A dialysis solution safe in application over the complete shelf life of the product, preferably over a period of 24 months or longer, can thus be ensured. This furthermore results in a substantial gain in safety on use of the dialysis solution at a dialysis machine.

The term "dialysis solution" in the present case comprises both concentrates which have to be further diluted prior to use and ready-to-use solutions which can be used as such as part of the dialysis. Both dialysis solutions and substitution solutions for hemodialysis, hemodiafiltration and hemofiltration and solutions for peritoneal dialysis are covered.

The organic ester of phosphoric acid can, for example, be an organic ester of orthophosphoric acid, preferably an organic monoester of orthophosphoric acid. The organic ester of phosphoric acid can, for example, be in the form of a salt of an organic ester of phosphoric acid.

In one embodiment, the organic ester of orthophosphoric acid is glycerol orthophosphate. This substance is already established as an active substance, for example, for parenteral nutrition and is also monographed in the European Pharmacopoeia (01/2009:1995). This relatively small molecule can be metabolized quickly while releasing orthophosphate. The glycerol-orthophosphate can be a glycerol-2-orthophosphate, a glycerol-3-orthophosphate or a mixture thereof.

The organic ester of phosphoric acid can be contained, for example, in a concentration of up to 3 mmol/L, up to 1.5 mmol/L, up to 1.25 mmol/L, or up to 1.2 mmol/L, with respect to the phosphate in the ready-to-use solution. The organic ester of phosphoric acid can furthermore be contained in a minimal concentration of 0.5 mmol/L or more, of 0.8 mmol/L or more, or of 1 mmol/L or more, with respect to the phosphate in the solution. If the organic ester of phosphoric acid is a monoester such as glycerol-orthophosphate, the concentration "with respect to the phosphate" corresponds to the concentration of the ester overall.

In an embodiment, the dialysis solution contains the organic ester of phosphoric acid in a concentration of 0.65 to 1.45 mmol/L, 0.8 to 1.25 mmol/L, or of 1 to 1.2 mmol/L, with respect to the phosphate. A phosphate concentration of 0.8 to 1.25 mmol/L, or from 1 to 1.2 mmol/L, corresponds to a concentration which can be used to regulate the phosphate balance of dialysis patients and to prevent hypophosphatemia, for example. Not only is the solution stabilized by the addition of the organic ester of phosphoric acid, but a desirable physiological effect is also achieved.

In some embodiments, the dialysis solution contains orthophosphate in addition to the organic ester of phosphoric acid. It has been found that on the addition of both an organic ester of phosphoric acid and of orthophosphate, a synergistic effect occurs which results in an even better stabilization of the solution with respect to the precipitation of calcium carbonate.

In certain embodiments, orthophosphate is contained in addition to the organic ester of phosphoric acid in a concentration of >0 to 0.3 mmol/L, 0.1 to 0.3 mmol/L, or of 0.1 to 0.2 mmol/L. The synergistic effect can be observed as very pronounced in these concentration ranges and the total content of the phosphate is additionally in the physiological range.

In some embodiments, the dialysis solution contains further electrolytes, such as sodium ions, potassium ions and/or chloride ions, in addition to the calcium ions and/or magnesium ions.

In an embodiment, the dialysis solution also contains at least one osmotic agent, such as a saccharide or a saccharide derivative. Examples of saccharides and saccharide derivatives include glucose and glucose derivatives. In some embodiments the solution contains up to 2 g/L of glucose.

The named solvates can be present in the dialysis solution independently of one another, for example in the following concentrations:

TABLE 1

| | |
|---|---|
| Calcium ions: | 1-2 mmol/L, for example 1.5 mmol/L |
| Magnesium ions: | 0.2-0.8 mmol/L, for example 0.5 or 0.75 mmol/L |
| Potassium ions: | Up to 8, and preferably up to 4 mmol/L |
| Sodium ions: | 120-160 mmol/L, for example 140 mmol/L |
| Bicarbonate ions (incl. carbonate ions and dissolved $CO_2$): | 30-40 mmol/L, for example 35 mmol/L |
| Osmotic agent: | 4-12 mmol/L, for example 5.6 mmol/L |
| Chloride ions: | 100-120 mmol/L, for example 109 mmol/L |

In certain embodiments, the pH of the dialysis solution is in the range from 7.0 to 7.6.

Aspects of the invention further relate to a combination of several, e.g. exactly two, individual solutions which are configured such that they form a dialysis solution of the type described herein after their mixing with one another.

In some embodiments, only one of the individual solutions contains the organic ester of phosphoric acid and optionally the orthophosphate.

In certain embodiments, a first individual solution contains calcium ions and/or magnesium ions and a second individual solution which does not contain any calcium ions and/or magnesium ions contains the organic ester of phosphoric acid and optionally the orthophosphate.

In certain embodiments, a first individual solution contains calcium ions and/or magnesium ions, chloride ions, an osmotic agent and optionally potassium, and a second individual solution contains sodium ions, chloride ions, bicarbonate ions, the organic ester of phosphoric acid and optionally the orthophosphate.

In some embodiments, the first individual solution contains no bicarbonate ions and/or no organic esters of phosphoric acid and/or no orthophosphate and/or no sodium ions.

In certain embodiments, the second individual solution contains no calcium ions and/or magnesium ions and/or no potassium ions and/or no osmotic agent.

The named solvates can be present in the respective individual solution independently of one another, for example in the following concentrations:

TABLE 2

| | |
|---|---|
| Calcium ions: | 20-40 mmol/L, for example 30 mmol/L |
| Magnesium ions: | 5-15 mmol/L, for example 10 mmol/L |
| Potassium ions: | Up to 100 mmol/L |
| Sodium ions: | 100-200 ml/L, for example 140-160 mmol/L or exactly 147.5 mmol/L |
| Bicarbonate ions (incl. carbonate ions and dissolved $CO_2$): | 30-50 mmol/L, for example 37 mmol/L |
| Osmotic agent: | 100-250 mmol/L, for example 111 mmol/L |
| Chloride ions: | 60-100 mmol/L or 100-120 mmol/L |
| Organic esters of phosphoric acid (with respect to | more than 0.5 mmol/L, for example 0.5-3 mmol/L or 0.8-1.25 mmol/L |

TABLE 2-continued

| | |
|---|---|
| the phosphate) | |
| Orthophosphate or orthophosphoric acid (where present) | >0-0.3 mmol/L, for example 0.1-0.2 mmol/L |

Chloride ions can be present in both individual solutions, for example. The chloride ion concentration in an individual solution which contains the osmotic agent can in this respect be in a concentration range from 60 mmol/L to 100 mmol/L, and can be, for example, at exactly 82 mmol/L and, in an individual solution which contains the buffer and/or the organic ester of phosphoric acid, can be in a concentration range from 100 mmol/L to 120 mmol/L, and can be, for example, exactly 110 mmol/L.

In some embodiments, a first individual solution has a pH in the range from 2.4 to 3.0 and a second individual solution containing the organic ester of phosphoric acid has a pH in the range from 7.0 to 7.8.

In certain embodiments, the combination has two individual solutions A and B, wherein the solution A has one, a plurality of or all of the aforesaid characteristics of a first individual solution, and/or wherein the solution B has one, a plurality of or all of the aforesaid characteristics of a second individual solution.

Some aspects of the invention relate to a multi-chamber bag comprising at least two chambers, wherein one of the chambers has a first individual solution and another chamber has a second individual solution. The first and second individual solutions can be solutions of the type described above. The multi-chamber bag can have at least one separating means which separates different chambers from one another. The separating means can, for example, be a weld seam. The separating means or the weld seam can be configured such that it is opened by pressure on one of the chambers such that a connection arises between the separated chambers.

EXAMPLES

Embodiments of the invention are further described in the following examples, which do not limit the scope of the invention described in the claims.

Example 1

Increasing the Stability of Dialysis Solutions

A decisive advantage of the dialysis solutions described herein is an increase in the stability of the dialysis solution with respect to precipitations in comparison with known dialysis solutions of the category having comparable physiological effects.

Figure 2:
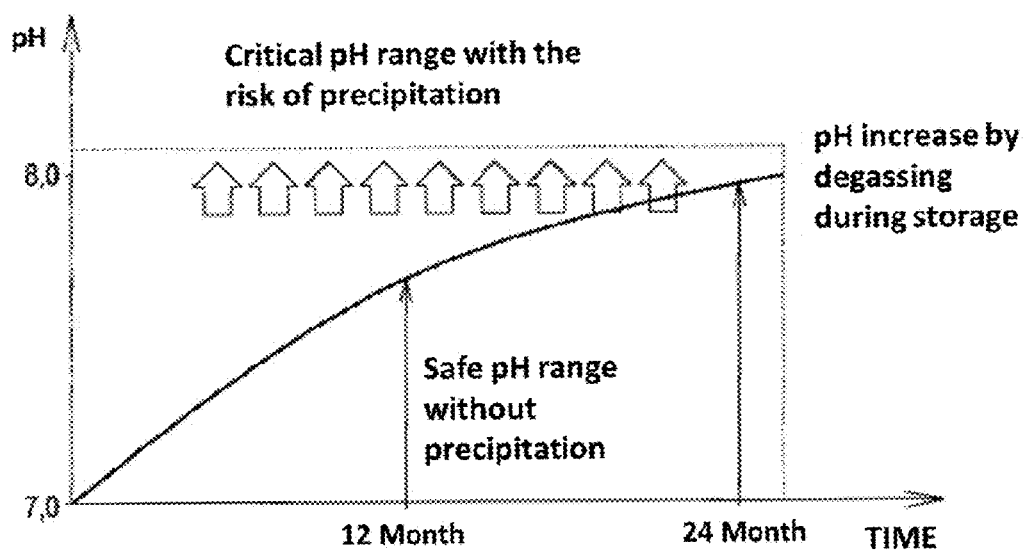
FIG. 2 is a schematic representation of safe and critical pH ranges of a bicarbonate-buffered solution with improved stability.

This effect is shown in the schematic representations of safe and critical pH ranges in accordance with FIGS. 1 and 2. FIG. 1 illustrates the corresponding ranges for a bicarbonate-buffered solution of the prior art. FIG. 2 illustrates the corresponding ranges for a bicarbonate-buffered solution with improved stability.

The characteristic line in FIG. 1 shows the curve of the pH over the storage duration. There is a safe region beneath a pH of approximately 7.5 in which no precipitation of calcium ions or magnesium ions as carbonate or phosphate takes place with a bicarbonate-buffered solution of the prior art. There is a critical range above a pH of approximately 7.5 in which such a precipitation takes place as soon as the metastable state collapses with a bicarbonate-buffered solution of the prior art.

The safe range is expanded to higher pH values in a bicarbonate-buffered solution with improved stability (FIG. 2) with respect to the prior art solution (FIG. 1). Whereas the solution of the prior art therefore departs from the safe range (FIG. 1) after a specific storage time (approximately 12 months in the present example), the stabilized solutions dwells substantially longer in the safe range (more than 24 months in the present case).

Example 2

Detecting the Stability of a Solution

The "Rapid-Controlled Precipitation Method" or the "Critical pH Method" can be used for determining the stability of the dialysis solution such as is described in F. Hui et al: Journal European of Water Quality (Journal European d'Hydrologie) T.33 Fasc. 1 (2002).

The results described within the framework of this disclosure were obtained by a modified rapid controlled precipitation method. The experiment setup comprises six 3-neck flasks (Carousel-6 from Radleys) which are open toward the top to ensure a uniform degassing of $CO_2$ from the solution. Furthermore, this setup allows an in-line measurement of e.g. the pH and the conductivity as well as the simultaneous heating of the flasks.

The basic principle of the method used comprises the pH of the mixed solution or of the dialysis solution being slowly raised by controlled degassing of $CO_2$ until the dialysis solution reaches a metastable state and ultimately precipitates.

A pH measurement, a particle count or a turbidity measurement can be used, for example, as methods for detecting the precipitation. It is recommended to carry out an in-line measurement in this respect in order precisely to detect the exact time of the start of precipitation and not to falsify detection by a sample preparation and transport to the analysis device. The measured curves which can be obtained using these methods are compared in FIG. 3.

Figure 3:
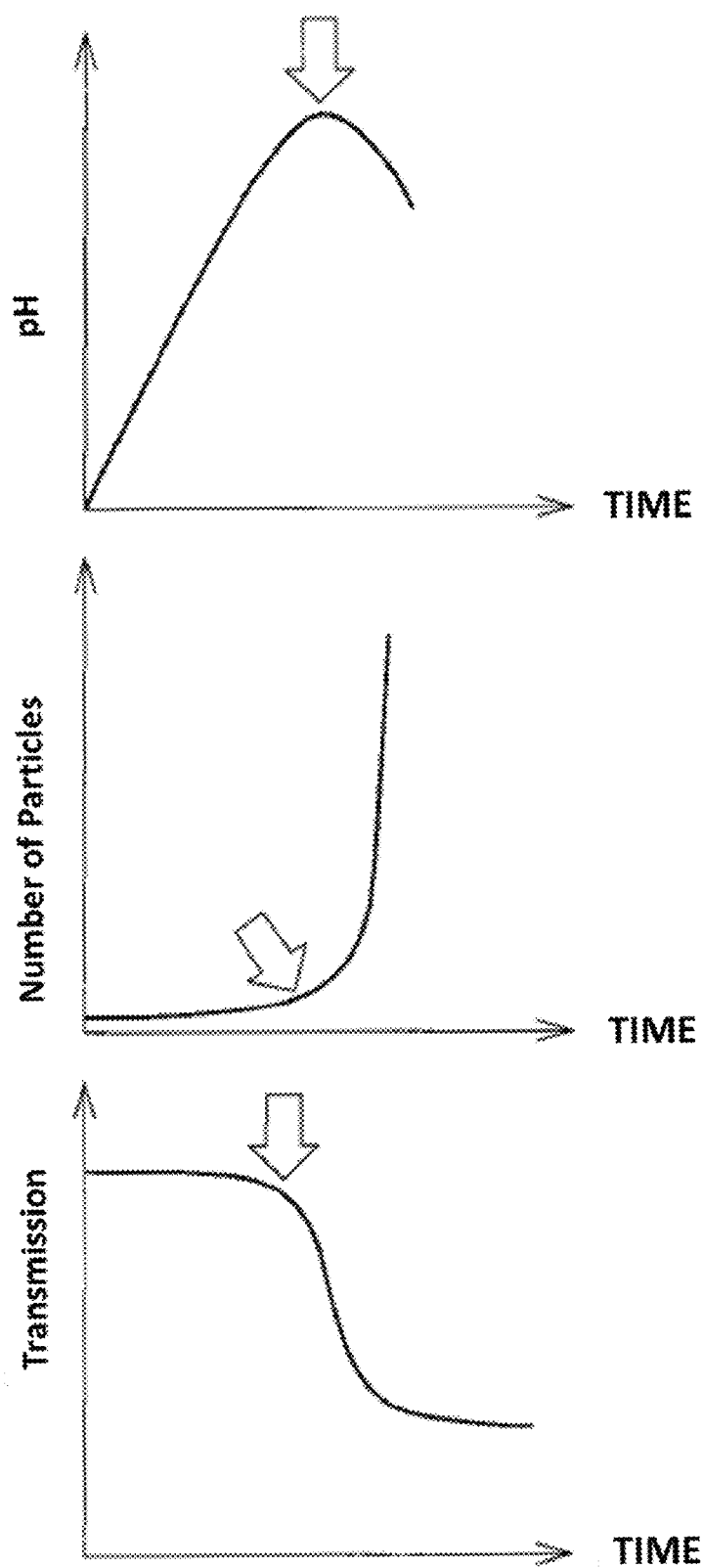
FIG. 3 is a schematic representation of the analytical methods of detecting precipitation in dialysis solutions (TOP—pH value, MIDDLE—# of particles, BOTTOM—Turbidity measurement).

In the case of a pH measurement, the start of the carbonate precipitation can be recognized by a significant bump in the curve of the pH value (FIG. 3, left hand illustration). Considered over time, the pH increases by the degassing of $CO_2$ and reaches a maximum ($pH_{max}$) at which the precipitation reaction starts. In many cases, this $pH_{max}$ value can be used as a criterion for the stability of a dialysis solution. The start of the precipitation can be recognized in the particle measurement by an increase in the number of particles (FIG. 3, middle illustration); it can be recognized in the turbidity measurement by a fall in the transmission (FIG. 3, right hand illustration). The time of the start of precipitation is called $t_G$ (time of germination).

The higher the $pH_{max}$ value, the higher the stability of the solution. A higher stability also means larger $t_G$ times under the same degassing conditions. The key values with respect to the solution stability are shown clearly in FIG. 4 for the example of a degassing experiment with calcium carbonate precipitation.

Figure 4:
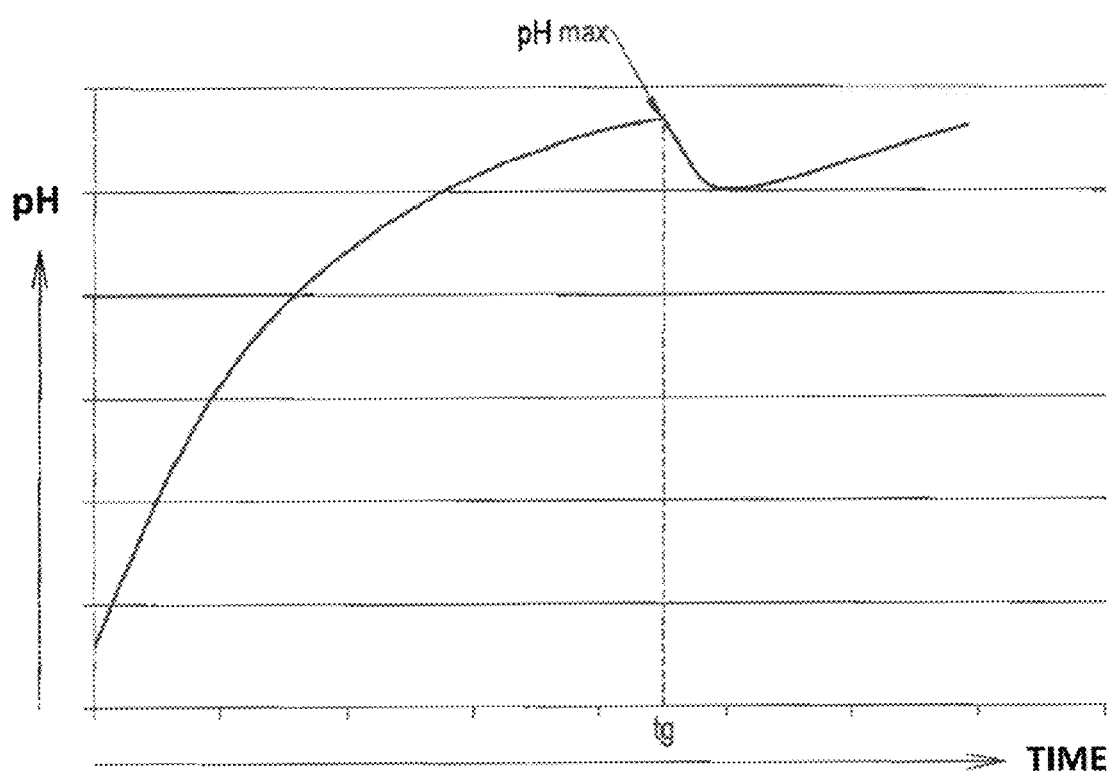
FIG. 4 is a schematic representation of the pH of a dialysis solution in temporal progression of a degassing experiment.

In FIG. 4, the increase in the pH up to the time $t_G$ can be explained by the degassing of $CO_2$ from the dialysis solution. As can furthermore be seen from FIG. 4, a local $pH_{max}$ arises. After this point, oversaturation of the dialysis solution occurs and a precipitation of calcium carbonate takes place. Carbonate ions are removed from the dialysis solution on the precipitation. The pH drops and protons are increasingly formed due to the equilibrium reaction with bicarbonate, which results in the drop in the pH.

The stability of the dialysis solution or of an individual solution can be significantly increased by the addition of an organic ester of phosphoric acid, with the collapse of the metastable range being delayed or prevented in full.

Example 3

Comparing the Stability of a Solution with Orthophosphate

Orthophosphate in a physiological concentration is added to a bicarbonate-buffered dialysis solution containing calcium ions and/or magnesium ions.

If 1.0 mmol/L orthophosphate is added to a conventional "multiBic"0K solution of the company Fresenius Medical Care Deutschland GmbH while maintaining the remaining solution components, it can be recognized from the comparison of the unmodified solutions and the orthophosphate ("P") modified solutions that the "multiBic" solution achieved a $t_G$ time of approximately 2 hours. The addition of 1.0 mml/L orthophosphate results in a stabilization of the solution and the $t_G$ time is increased to just over 6.5 hours.

Figure 5:
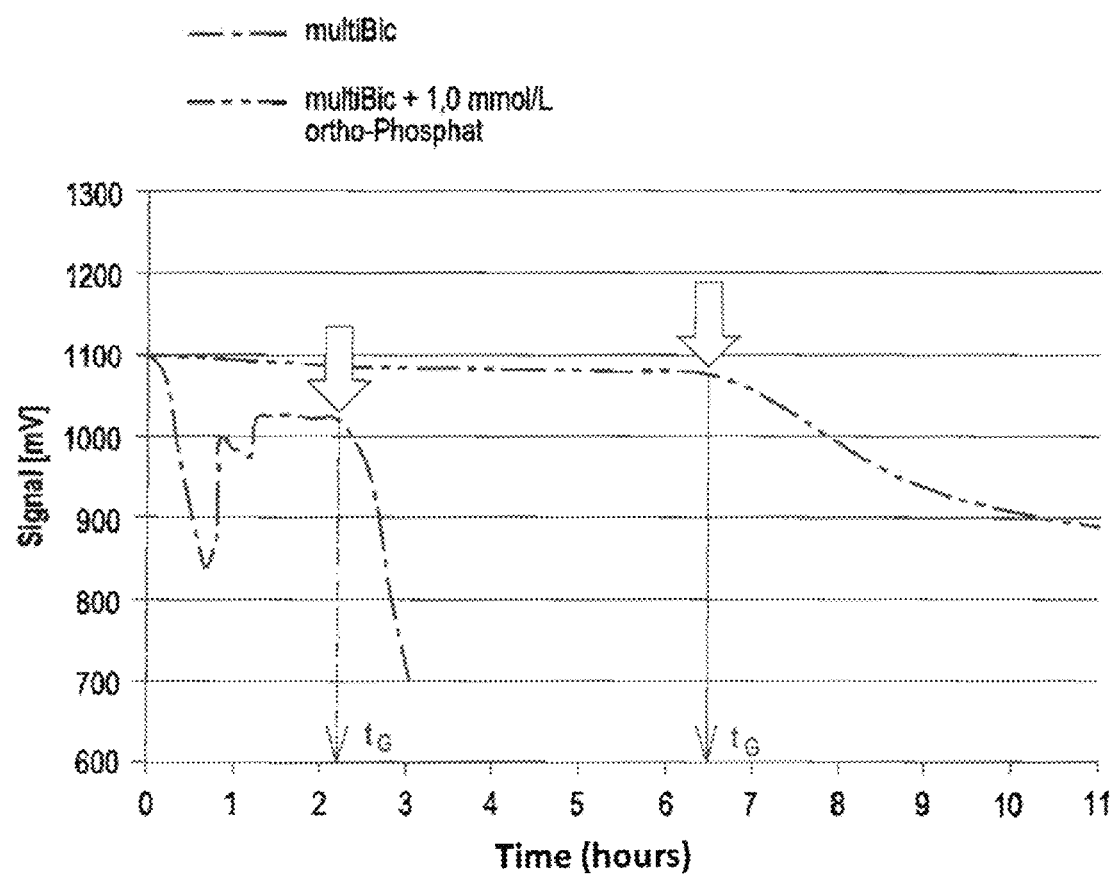
FIG. 5 is a representation of the turbidity of two dialysis solutions in the temporal progression of a degassing experiment.

FIG. 5 shows the corresponding measured curves which were obtained using the rapid controlled precipitation method at T=40° C. using the turbidity measurement as detection.

Figure 6:
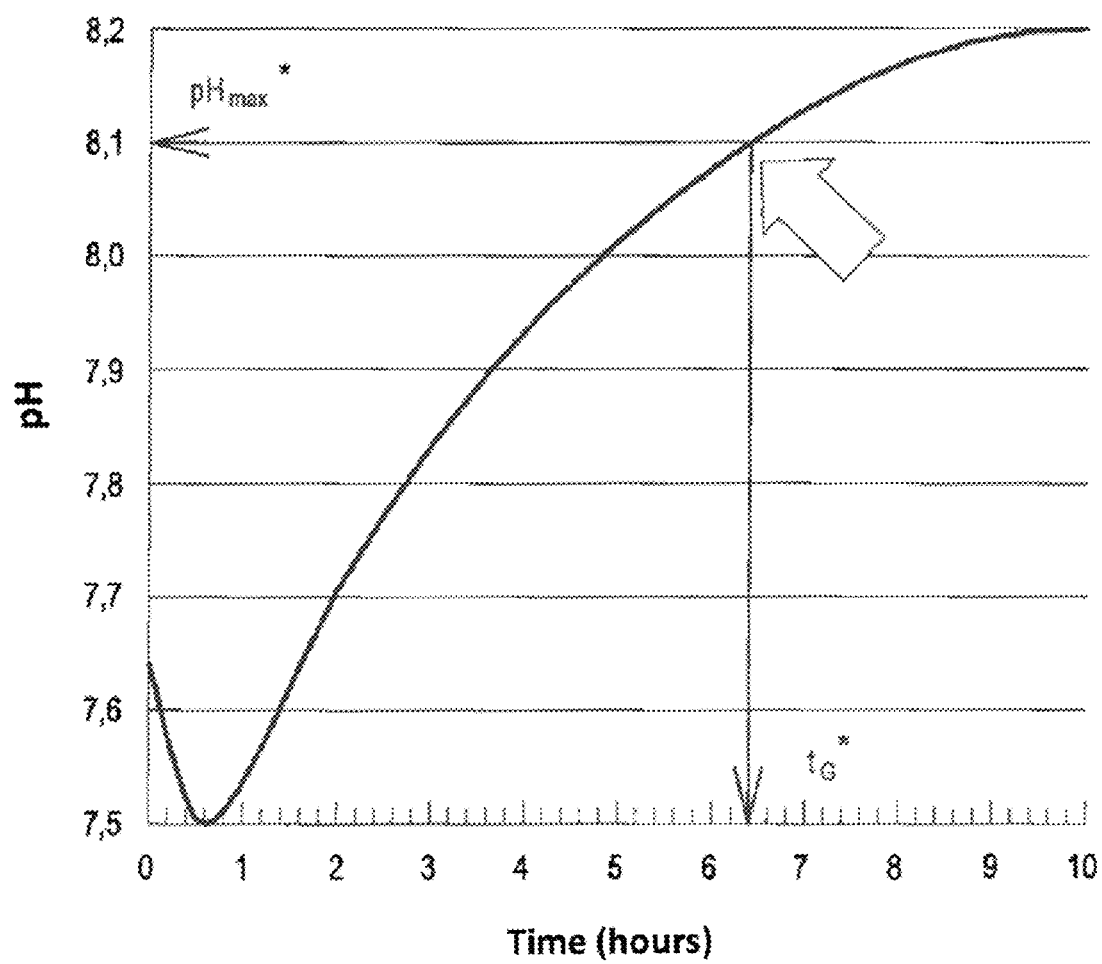
FIG. 6 is a representation of the pH of a dialysis solution containing phosphate in the temporal progression of a degassing experiment.

The pH measured curve of a corresponding measurement at the P-modified "multiBic" solution shown in FIG. 6 interestingly does not show any significant bump in the curve of the pH value and is therefore not suitable to detect the precipitation. The $pH_{max}$ values in this case therefore had to be derived from the $t_G$ values determined by particle measurement or by turbidity measurement.

Figure 7:
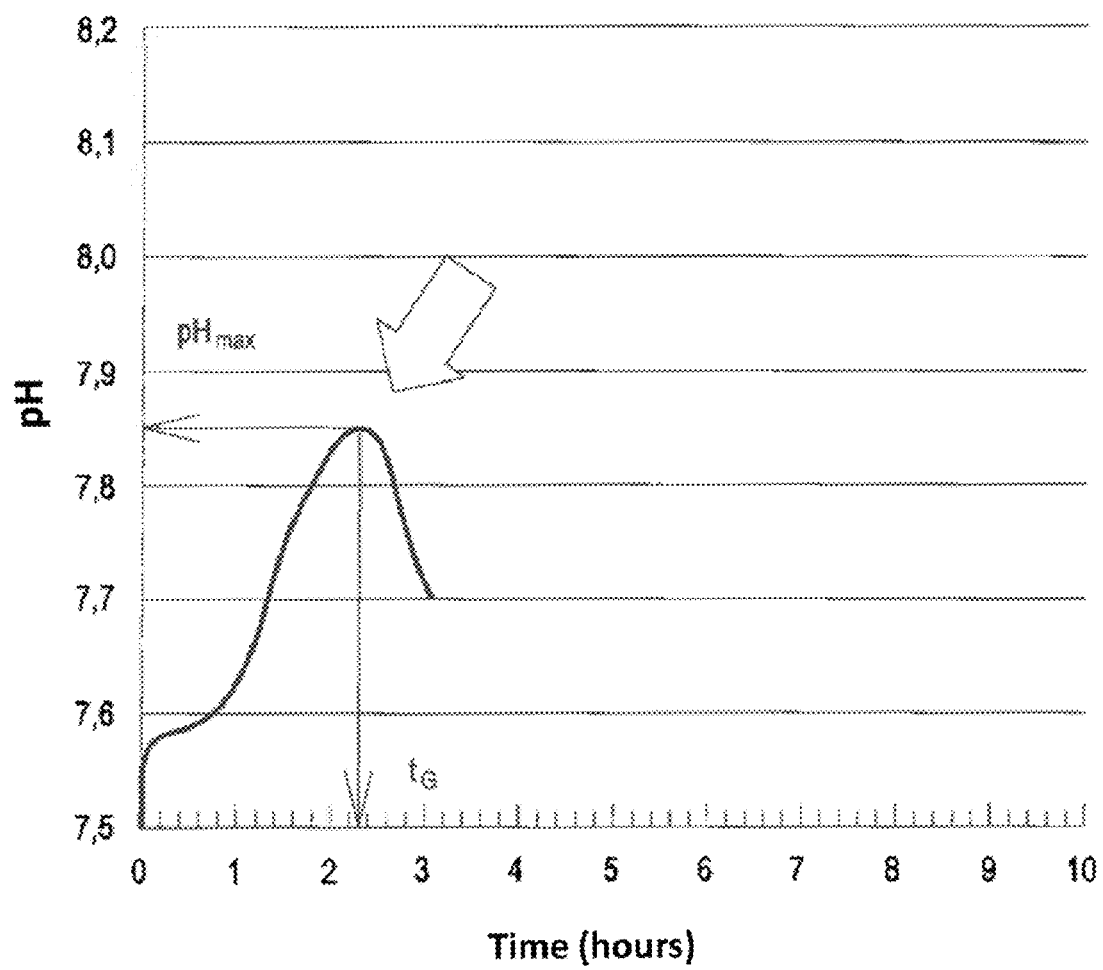
FIG. 7 is a representation of the pH of a dialysis solution free of phosphate in the temporal progression of a degassing experiment.

The pH measured curve of the phosphate-free unmodified "multiBic" solution shown in FIG. 7, in contrast, shows the customary image of the significant drop at the start of precipitation. The $pH_{max}$ value here is 7.85. The $t_G$ value coincides well with the value from the turbidity measurement.

Figure 8:
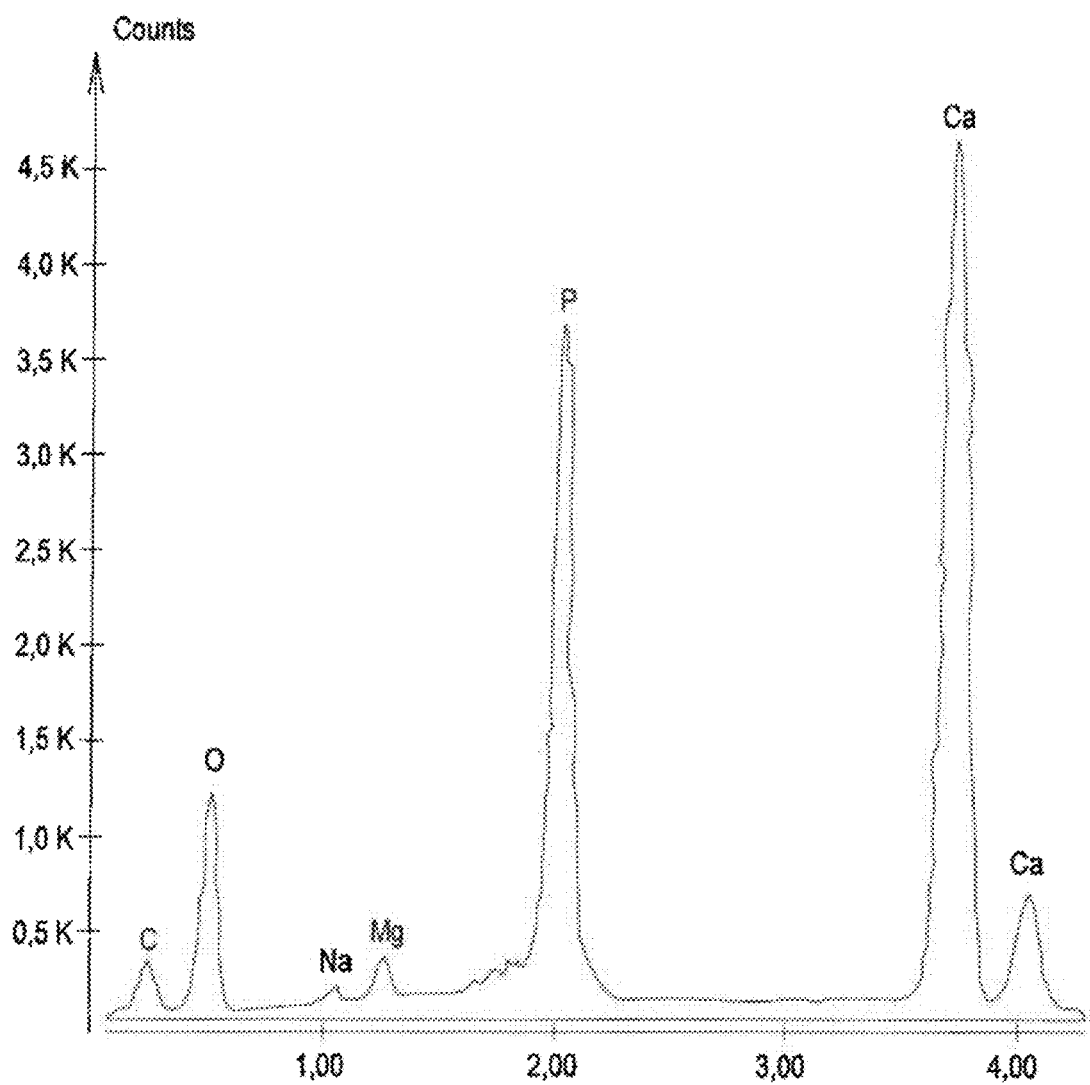
FIG. 8 is an energy-dispersive X-ray (EDX) spectrum of the isolated precipitation product of a dialysis solution containing phosphate.
Figure 9:
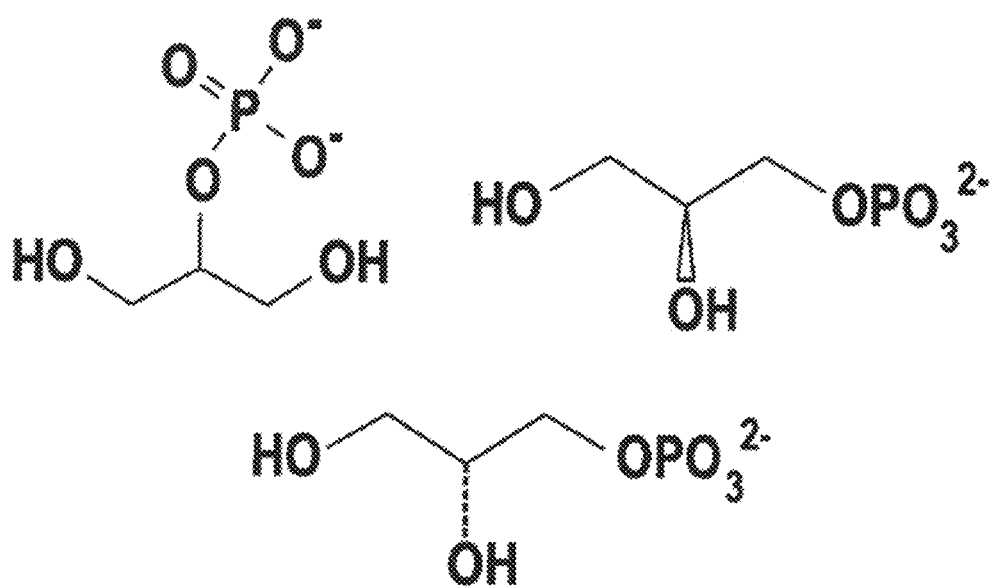
FIG. 9 is the structural formulas of glycerol-2-orthophosphate and glycerol-3-orthophosphate.

This behavior of the P-modified "multiBic" solution is indicative of the fact that another phase of low solubility is forming. This assumption is confirmed by an EDX spectrum shown in FIG. 8 which clearly shows that a calcium phosphate compound arises as the main product for the OP-modified "multiBic" solution with a physiological phosphate concentration.

The precipitate could, for example, be a calcium hydrogen phosphate which is formed in accordance with the following equation:

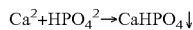

Since no protons are released in this reaction, no drop in the pH signal can be recognized either, which would explain the lack of the significant pH kink.

The precipitation of calcium carbonate in contrast releases protons; the precipitation can in this case be detected by means of pH measurement:

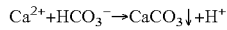

The compositions and pH values of the unmodified "multiBic" solution of the P-modified "multiBic" solution, of a conventional "multiPlus" solution containing phosphate of Fresenius Medical Care and of a conventional "Phoxilium" solution containing phosphate of Gambro are shown in the following Table 3 (the values given are manufacturer's data):

TABLE 3

|  | Unmodified "multiBic" solution. | P-modified "multiBic" solution. | "multiPlus" solution | "Phoxilium" solution |
|---|---|---|---|---|
| $Na^+$ | 140 | 140 | 140 | 140 |
| $K^+$ | 0 | 0 | 2 | 4 |
| $Mgz^{2+}$ | 0.50 | 0.50 | 0.75 | 0.60 |
| $Ca^{2+}$ | 1.50 | 1.50 | 1.50 | 1.25 |
| $Cl^-$ | 109.0 | 109.0 | 110.5 | 115.9 |
| $HCO_3^-$ | 35 | 35 | 35 | 30 |
| $HPO_4^{2-}$ | 0 | 1.0 | 1.0 | 1.2 |
| Glucose | 5.55 | 5.55 | 5.55 | 0 |
| pH | ~7.4 | ~7.4 | ~7.4 | ~7.4 |

The "Phoxilium" solution contains the highest phosphate concentration at 1.20 mmol/L, but no glucose and the lowest concentrations of calcium and bicarbonate. The magnesium concentration is furthermore increased in the "Phoxilium" solution and in the "multiPlus" solution.

The $pH_{max}$ and the precipitation products of the different solutions are compiled in Table 4 shown in the following. The values were all determined at 40° C. using the "rapid degassing" method.

TABLE 4

|  | $pH_{max}$ | Precipitation product: |
|---|---|---|
| Unmodified "multiBic" Solution | 7.9 | Calcium carbonate |
| P-modified "multiBic" solution | 8.3* | Calcium phosphate |
| "multiPlus" solution | 8.3* | Calcium phosphate |
| "Phoxilium" solution | 8.2* | Calcium phosphate |

*derived from turbidity measurement and/or particle measurement

The stability measurements show that the presence of orthophosphate increases the stability of the solution with respect to the precipitation reaction, but has the decisive disadvantage that calcium phosphate occurs as the precipitation product. If particles are precipitated and infused in a treatment with these solutions containing phosphate despite all the precautionary measures, this would presumably have more serious consequences than with a solution containing pure bicarbonate without a phosphate additive.

The special composition of e.g. the "Phoxilium" solution furthermore has the disadvantage that the smaller calcium and bicarbonate concentrations can manifest negatively in a CRRT treatment, whereby hypocalcemia and acidosis can occur in the patients (Journal of Critical Care, 28, 5, 2013, 884.e7-884.e14).

Example 4

Increasing the Stability with Glycerol-Orthophosphate

The present disclosure suggests phosphate sources which are absorbed fast by the body, which stabilize the solution and which do not form any phosphates which are of low solubility.

This will be illustrated in the following with reference to the addition of a mixture of glycerol-2-orthophosphate and glycerol-3-orthophosphate (hereinafter simply "glycerol-orthophosphate") to a dialysis solution. This substance is a representative of the organic esters of phosphoric acid. FIG.

9 shows the structural formulas of the glycerol-2-orthophosphate and of the glycerol-3-orthophosphate.

Figure 10:
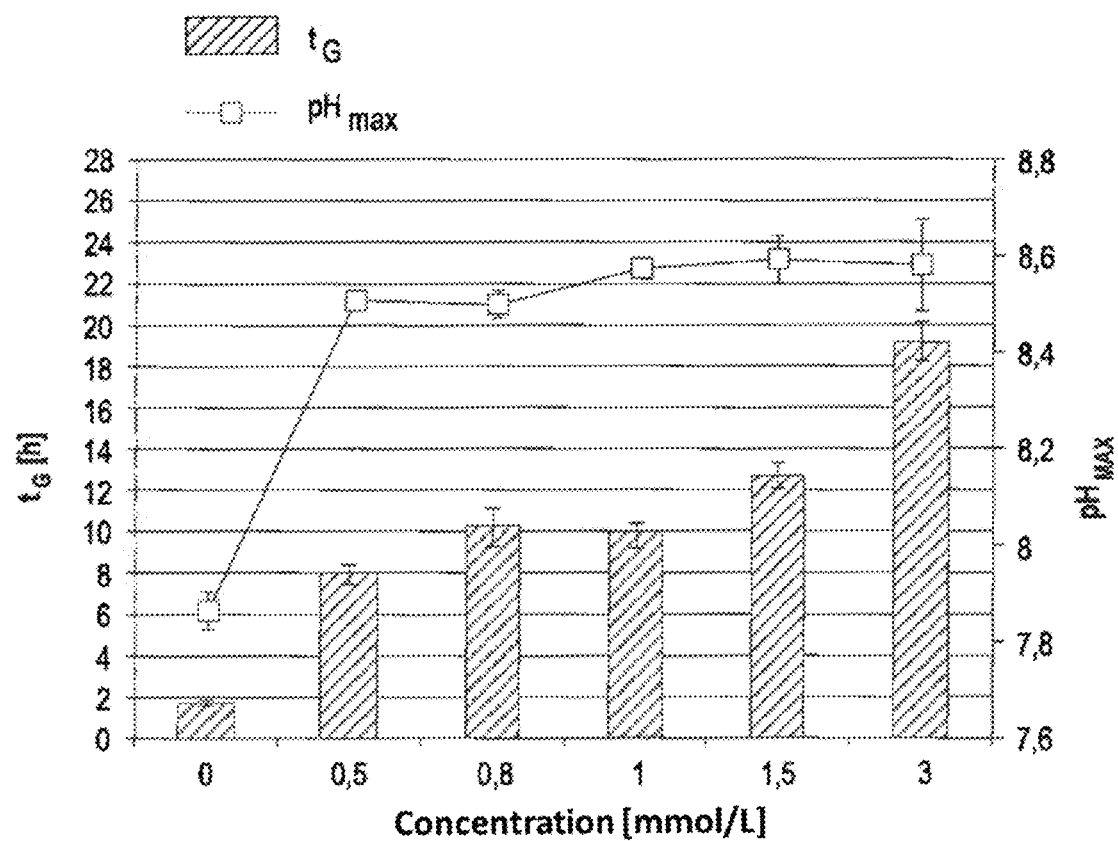
FIG. 10 is a representation of the $pH_{max}$ values and $t_G$ values of dialysis solutions having different concentrations of glycerol-2-orthophosphate. $pH_{max}$ is the pH at which the precipitation reaction starts and $t_G$ is the time of germination or the time of the start of the precipitation reaction.

The stability of a plurality of "multiBic" solutions admixed with different concentrations of glycerol-orthophosphate is shown in FIG. 10. As can be seen from this, both $pH_{max}$ and the $t_G$ values of the solution increase as the concentration of glycerol-orthophosphate increases. It is noteworthy in this respect that the $pH_{max}$ is already considerably increased at a concentration of 0.5 mmol/L with respect to a conventional "multiBic" solution. The solution also has a considerable gain in stability in the physiologically relevant range from 0.8 to 1.25 mmol/L.

Figure 11:
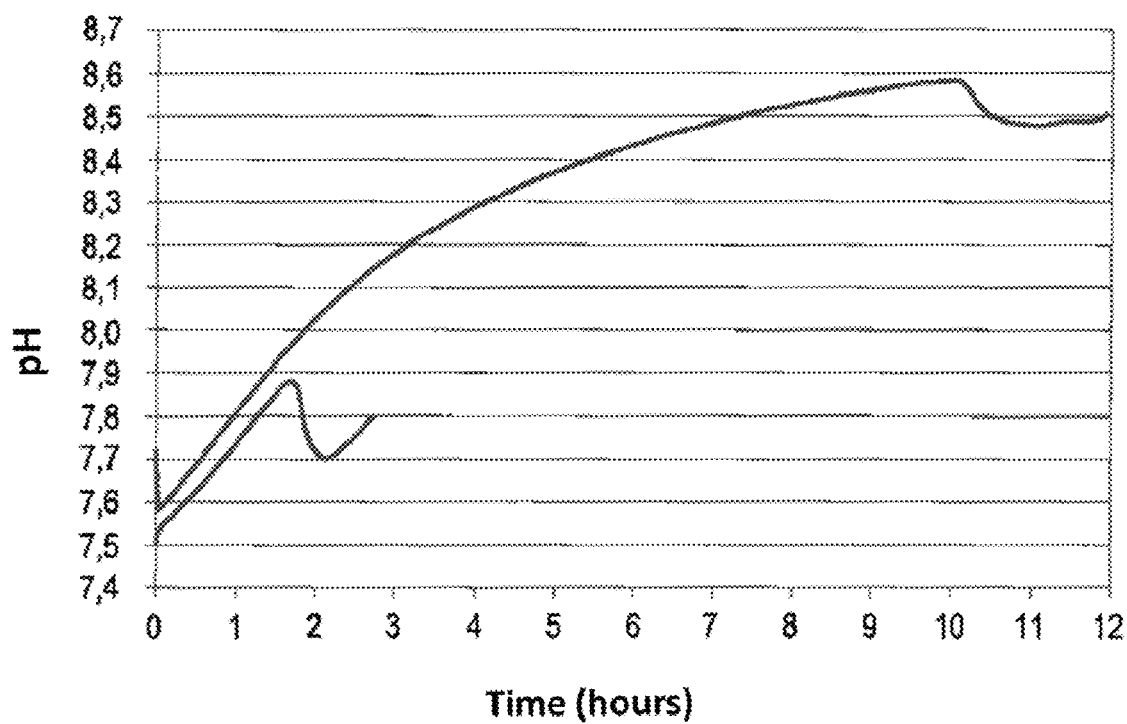
FIG. 11 is a representation of the pH values of two dialysis solutions in the temporal progression of a degassing experiment.

The pH curve shown in FIG. 11 furthermore indicates that, in the case of a precipitation at high pH values (upper curve), only calcium carbonate arises as a compound low in solubility since the typical curve progression with a significant drop in the pH can be recognized at the start of the precipitation (analog to a conventional "multiBic" solution, lower curve). This assumption can also be confirmed by a determination of the phosphate content by means of UV-vis spectroscopy (enzymatic test kit).

If the values of a P-modified "multiBic" solution shown in the following Table 5 in accordance with the comparison example are compared with the values of a "multiBic" solution admixed in accordance with this disclosure with 1 mmol/L glycerol orthophosphate ("GP"), it can be seen that in the P-modified "multiBic" solution the phosphate concentration after the precipitation is only −67% of the starting value, whereas in the GP-modified "multiBic" solution the phosphate content remains unchanged.

TABLE 5

|  | Phosphate content before precipitation [mg/L] | Phosphate content after precipitation [mg/L] |
| --- | --- | --- |
| P-modified solution | 30 | 21 |
| GP-modified solution | 22* | 22* |

*the absolute values of the measurement differ from the true value since no test kit specific to glycerol orthophosphate was used, but rather work was carried out using the test kit for orthophosphate.

A comparison of the $pH_{max}$ values of the GP-modified "multiBic" solution with the solutions containing orthophosphate of the comparison example furthermore shows that the $pH_{max}$ value of the solution is the highest with glycerol orthophosphate (Table 6).

TABLE 6

|  | pHmax | Precipitation product: |
| --- | --- | --- |
| Unmodified "multiBic solution | 7.9 | Calcium carbonate |
| P-modified "multiBic" solution | 8.3* | Calcium phosphate |
| "multiPlus" solution | 8.3* | Calcium phosphate |
| "Phoxilium" solution | 8.2* | Calcium phosphate |
| GP-modified "multiBic" solution | 8.6 | Calcium carbonate |

*derived from turbidity measurement and/or particle measurement

Figure 12:
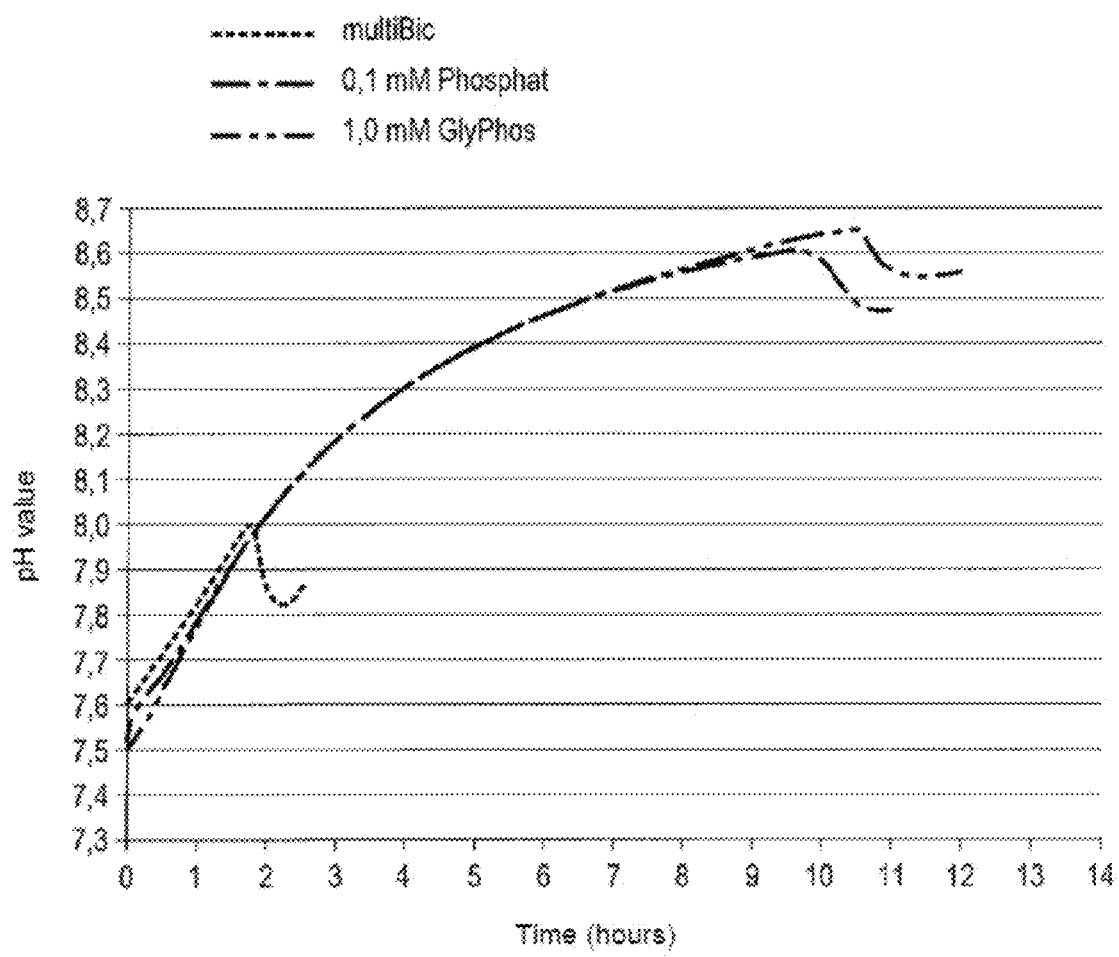
FIG. 12 is a representation of the pH values of three dialysis solutions in the temporal progression of a degassing experiment.

FIG. 12 shows a comparison of the stabilizing effect of glycerol orthophosphate in the physiological concentration range with that of orthophosphate. As can be seen from this, the addition of 1.0 mmol/L glycerol orthophosphate to the "multiBic" solution has almost the same stabilizing effect as the addition of 0.1 mmol/L orthophosphate. Furthermore, no phosphates low in solubility are formed as precipitation products on the addition of glycerol orthophosphate.

On the one hand, the required physiological concentration of phosphate can be provided in a dialysis solution by the addition of glycerol orthophosphate and at the same time the stability can be significantly increased in comparison with phosphate-free solutions or solutions containing orthophosphate. A dialysis solution, preferably an HF/HD solution having a physiological phosphate concentration is thus obtained by this recipe which has an improved shelf life and which can be used safely over a time period of e.g. 24 months.

Example 5

Increasing the Stability with Orthophosphate and Glycerol-Orthophosphate

Orthophosphate is furthermore added to the GP-modified "multiBic" solution from Example 4.

Figure 13:
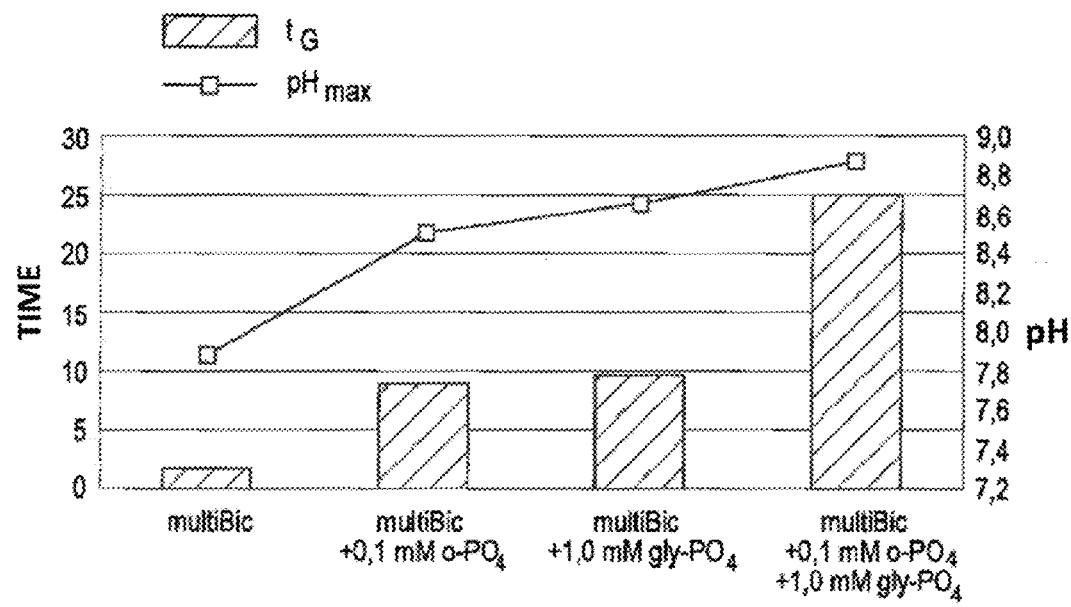
FIG. 13 is a representation of the $pH_{max}$ values and $t_G$ values of dialysis solutions having different concentrations of glycerol-2-orthophosphate and/or orthophosphate.

The stability of a plurality of the following solutions is shown in FIG. 13: Unmodified "multiBic solution in accordance with the comparison example; P-modified "multiBic" solution in accordance with the comparison example; GP-modified "multiBic" solution in accordance with Example 4 and a GP-modified "multiBic" solution additionally admixed with 0.1 mmol/L of orthophosphate. As can also be seen from FIG. 13, a disproportional increase in the stability results for the solution admixed both with glycerol orthophosphate and with orthophosphate with respect to the P-modified and the GP-modified "multiBic" solution.

The values were obtained as described above with reference to the "rapid controlled precipitation" method at T=40° C. with a pH measurement or, if not applicable, with a turbidity measurement and/or particle measurement as the detection.

Figure 14:
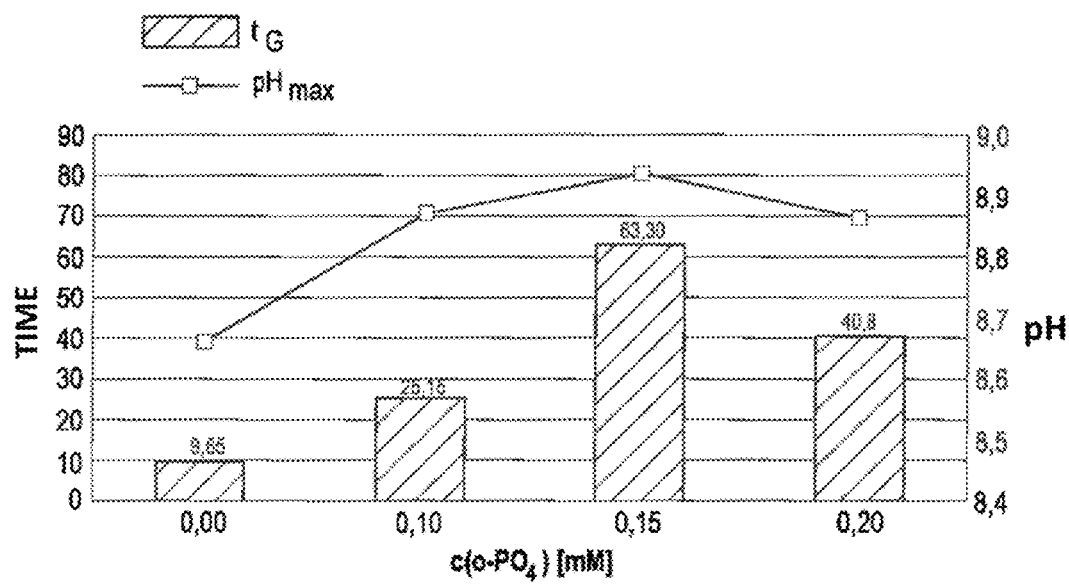
FIG. 14 is a representation of the $pH_{max}$ values and $t_G$ values of dialysis solutions with glycerol-2-orthophosphate and different concentrations of orthophosphate.

FIG. 14 shows the stability of a plurality of GP-modified "multiBic" solutions admixed with different concentrations of orthophosphate. As can be seen from this, a stability maximum is reached corresponding to a maximum $pH_{max}$ value with an addition of 0.15 mmol/L orthophosphate.

Figure 15:
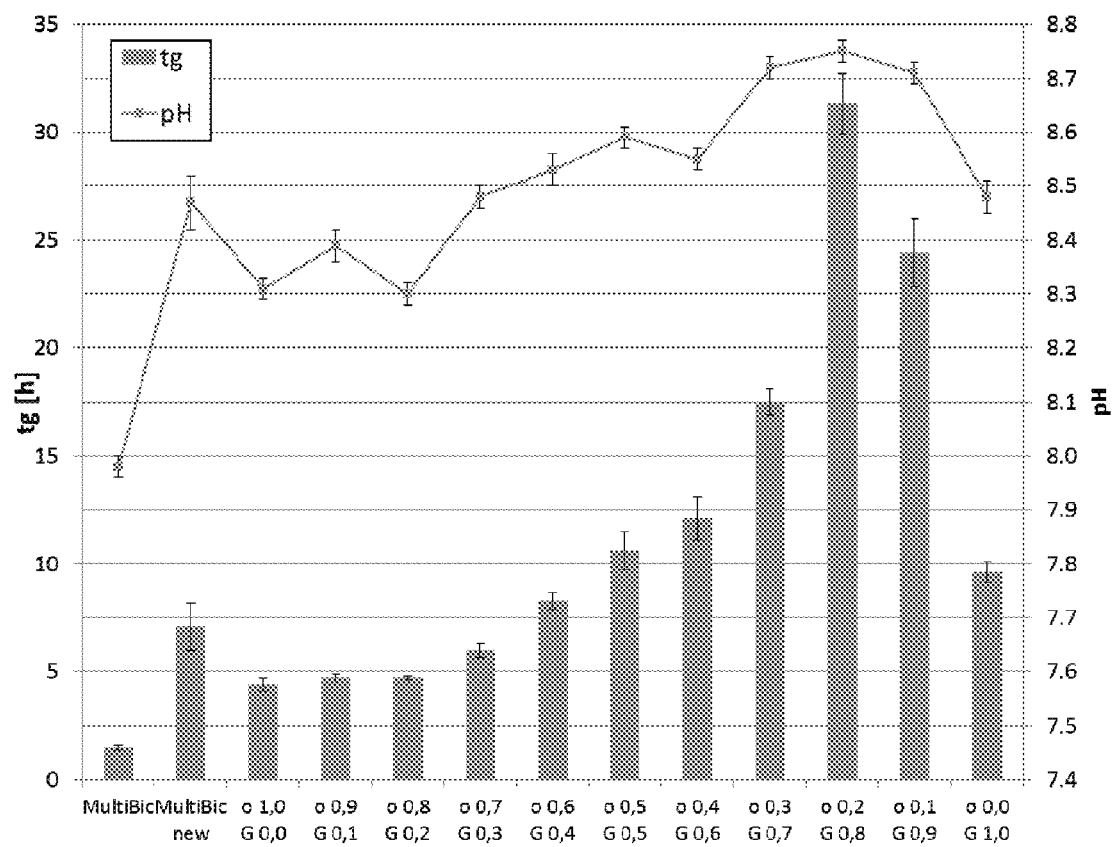
FIG. 15 is a representation of the $pH_{max}$ values and $t_G$ values of dialysis solutions with different concentrations of glycerol-2-orthophosphate and/or orthophosphate while keeping the total phosphate concentration at 1 mmol/l.

To further investigate the increase in stability for a solution containing both glycerol orthophosphate and orthophosphate (See FIG. 13), the stability of solutions with varying ratios of $H_3PO_4$/glycerol-phosphate were examined and the results are shown in FIG. 15. The $t_G$ and pH values were obtained at 40° C., while keeping the total phosphate concentration at 1 mmol/L. The results confirmed the synergistic effect of mixtures in the range of 0.3:0.7 to 0.1:0.9 (see FIG. 15).

The addition of organic esters of phosphoric acid, for example the addition of glycerol orthophosphate in physiological concentration ranges, results in a significant stabilization of bicarbonate-buffered dialysis solutions containing calcium ions and/or magnesium ions. Precipitation reactions can hereby be avoided up to pH values of pH>8, which considerably improves the safety and the durability of dialysis solutions.

The organic esters of phosphoric acid can act both as in-use stabilization agents and in medically relevant concentrations as a phosphate source for regulating the phosphate balance. An advantage with respect to commercial dialysis solutions is the considerably higher stability of the solution with respect to precipitation reactions of calcium carbonate (increased $pH_{max}$ values and respective $t_G$ times). A precipitation of calcium phosphate is avoided, unlike the solutions containing orthophosphate already on the market.

Additionally, a synergistic effect can be achieved by the addition of organic esters of phosphoric acid and further of orthophosphate which improves the described effects of the organic ester of phosphoric acid.

OTHER EMBODIMENTS

It is to be understood that while the invention has been described in conjunction with the detailed description of the various embodiments discussed above, the foregoing description is intended to illustrate and not limit the scope of the invention, which is defined by the scope of the appended claims. Other aspects, advantages, and modifications are within the scope of the following claims.

What is claimed is:

1. A dialysis solution, comprising:
   bicarbonate ions;
   one or more of calcium and magnesium ions; and
   an organic ester of phosphoric acid, wherein the organic ester of phosphoric acid is glycerol orthophosphate.

2. The dialysis solution of claim 1, wherein the concentration of the organic ester of phosphoric acid is 0.8 to 1.25 mmol/L with respect to the phosphate.

3. The dialysis solution of claim 2, wherein the concentration of the organic ester of phosphoric ester is 1 to 1.2 mmol/L with respect to the phosphate.

4. The dialysis solution of claim 1, further comprising one or more of an electrolyte and an osmotic agent, wherein the electrolyte is selected from the group consisting of sodium ions, potassium ions, and chloride ions, and wherein the osmotic agent is a saccharide or a saccharide derivative.

5. The dialysis solution of claim 1, further comprising orthophosphate, wherein the concentration of the orthophosphate is about 0.1 to 0.3 mmol/L.

6. The dialysis solution of claim 5, wherein the concentration of the orthophosphate is about 0.1 to 0.2 mmol/L.

7. The dialysis solution of claim 5, further comprising one or more of an electrolyte and an osmotic agent, wherein the electrolyte is selected from the group consisting of sodium ions, potassium ions, and chloride ions, and wherein the osmotic agent is a saccharide or a saccharide derivative.

8. A plurality of solution components to be mixed to form a solution, wherein the solution comprises:
   bicarbonate ions;
   one or more of calcium and magnesium ions;
   an organic ester of phosphoric acid; and
   optionally one or more of orthophosphate, an electrolyte, and an osmotic agent, wherein the organic ester of phosphoric acid is glycerol orthophosphate.

9. The plurality of solution components of claim 8, wherein the plurality of solution components comprise a first solution component and a second solution component, wherein the second solution component comprises the organic ester of phosphoric acid and optionally the orthophosphate.

10. The plurality of solution components of claim 9, wherein the first solution component is contained in a first chamber of a container, and the second solution component is contained in a second chamber of the container.

11. The plurality of solution components of claim 9, wherein the first solution component comprises one or more of calcium ions and magnesium ions; and the second solution component does not contain any calcium ions or magnesium ions.

12. The plurality of solution components of claim 11, wherein the first solution component further comprises chloride ions, an osmotic agent and optionally potassium ions; and wherein the second solution component further comprises sodium ions, chloride ions, and bicarbonate ions.

13. The plurality of solution components of claim 12, wherein the first solution component does not contain bicarbonate ions, organic esters of phosphoric acid, orthophosphate and sodium ions.

14. The plurality of solution components of claim 12, wherein the second solution component does not contain calcium ions, magnesium ions, potassium ions, and osmotic agents.

15. The plurality of solution components of claim 9, wherein the first solution component has a pH of about 2.4 to 3.0; and the second solution component has a pH of about 7.0 to 7.8.

* * * * *